US00PP20374P2

(12) United States Plant Patent
Álamo et al.

(10) Patent No.: US PP20,374 P2
(45) Date of Patent: Sep. 29, 2009

(54) BLUEBERRY PLANT NAMED 'ROCIO'

(50) Latin Name: ***Vaccinium corymbosum* L.**
Varietal Denomination: Rocio

(75) Inventors: Antonio Abad Álamo, Huelva (ES); José Ulf Hayler López, Huelva (ES); Paul M. Lyrene, Gainesville, FL (US)

(73) Assignee: Royal Berries S.L., Almonte, Huelva (ES)

( * ) Notice: Subject to any disclaimer, the term of this patent is extended or adjusted under 35 U.S.C. 154(b) by 0 days.

(21) Appl. No.: 12/213,085

(22) Filed: Jun. 13, 2008

(51) Int. Cl.
*A01H 5/00* (2006.01)

(52) U.S. Cl. ..... Plt./157
(58) Field of Classification Search ..... Plt./157
See application file for complete search history.

*Primary Examiner*—Annette H Para
(74) *Attorney, Agent, or Firm*—Buchanan Ingersoll & Rooney PC

(57) ABSTRACT

A new and distinct Blueberry cultivar is provided that is the product of a controlled breeding program followed by selection. The cultivar flowers very early and forms fruit that ripens very early. The attractive berries are extremely firm and exhibit an excellent balance of acid-sweetness. The plant is self-fertile and displays a generally vase to upright growth habit with attractive evergreen foliage. A low chilling requirement is also exhibited.

6 Drawing Sheets

Botanical/commercial classification: *Vaccinium corymbosum* L./Blueberry Plant.

Varietal denomination: cv. Rocio.

SUMMARY OF THE INVENTION

The new Blueberry cultivar of the present invention was the product of controlled artificial pollination carried out in a greenhouse at Greenwood, Fla., U.S.A., wherein two parents were crossed which previously had been studied in the hope that they would contribute the desired characteristics. The female parent (i.e., the seed parent) was the unreleased 'FL 96-24' cultivar (non-patented in the United States). The male parent (i.e., pollen parent) was unreleased 'FL 95-3' cultivar. The parentage of the new cultivar can be summarized as follows:

'FL 96-24'×'FL 95-3'.

The seeds resulting from the pollination were shipped to Almonte, Huelva, Spain, where they sown during approximately 1997, small plants were obtained which were physically and biologically different from each other and selective research of the progeny was carried out. Selective study resulted in the identification of a single plant of the new cultivar. The new plant initially was designated SO1-29-01.

It was found that the new Blueberry plant of the present invention displays the following combination of characteristics:

(a) flowers very early and forms fruit that ripens very early,
(b) displays a generally vase to upright growth habit with attractive evergreen foliage,
(c) is self-fertile,
(d) displays a low chilling requirement, and
(e) forms attractive extremely firm violet-blue berries that exhibit an excellent balance of acid-sweetness.

The new cultivar well meets the needs of the horticultural industry and can be grown to advantage for the commercial production of blueberries.

The new cultivar of the present invention can be distinguished from its ancestors and all other Blueberry cultivars known to its originators. When compared to the 'Sharpblue' cultivar (non-patented in the United States), the new cultivar forms substantially no fruit scar tears unlike the 'Sharpblue' cultivar. When compared to the 'Windsor' cultivar (U.S. Plant Pat. No. 12,783), the new cultivar tends to be taller and more upright while the 'Windsor' cultivar tends to display a more rounded growth habit. When compared to the 'Biloxi' cultivar (non-patented in the United States), the new cultivar is self-fertile and requires no external pollen source as does the 'Biloxi' cultivar. When compared to the 'Star' cultivar (U.S. Plant Pat. No. 10,675), the new cultivar ripens approximately four weeks earlier at Almonte, Huelva, Spain.

The new cultivar has been asexually reproduced by the rooting of cuttings beginning during the spring of 2001 at Almonte, Huelva, Spain. Such asexual propagation has shown that the characteristics of the new cultivar are firmly fixed and are stably transmitted from one generation to another. Accordingly, the new cultivar asexually reproduces in a true to type manner.

The new cultivar has been named 'Rocio'.

BRIEF DESCRIPTION OF THE PHOTOGRAPHS

The accompanying photographs show in color as nearly true as it is reasonably possible to make the same in color illustrations of this character, a typical plant and plant parts of the new cultivar. The plant which had been asexually reproduced by the rooting of a cutting was approximately five years of age except where otherwise indicated, and was being grown outdoors at Almonte, Huelva, Spain. All photographs were obtained during March–April, 2008 except where otherwise indicated.

FIG. 1 shows an overall view of a typical fruiting plant of the new cultivar.

FIG. 2 was obtained on Feb. 8, 2008 and shows a close view of the flowers of the new cultivar in various stages of opening.

DETAILED DESCRIPTION

Figure 1:
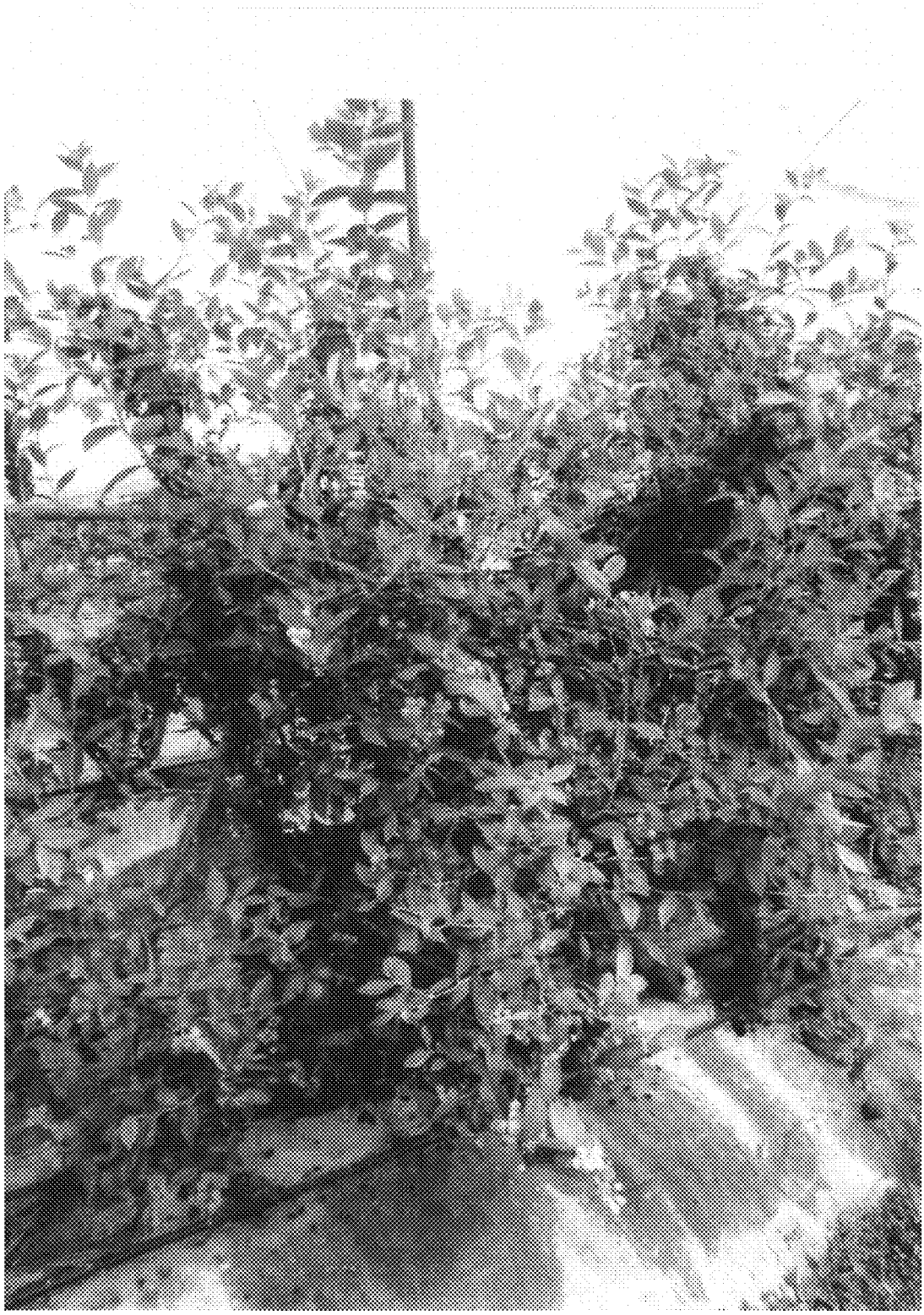
Figure 2:
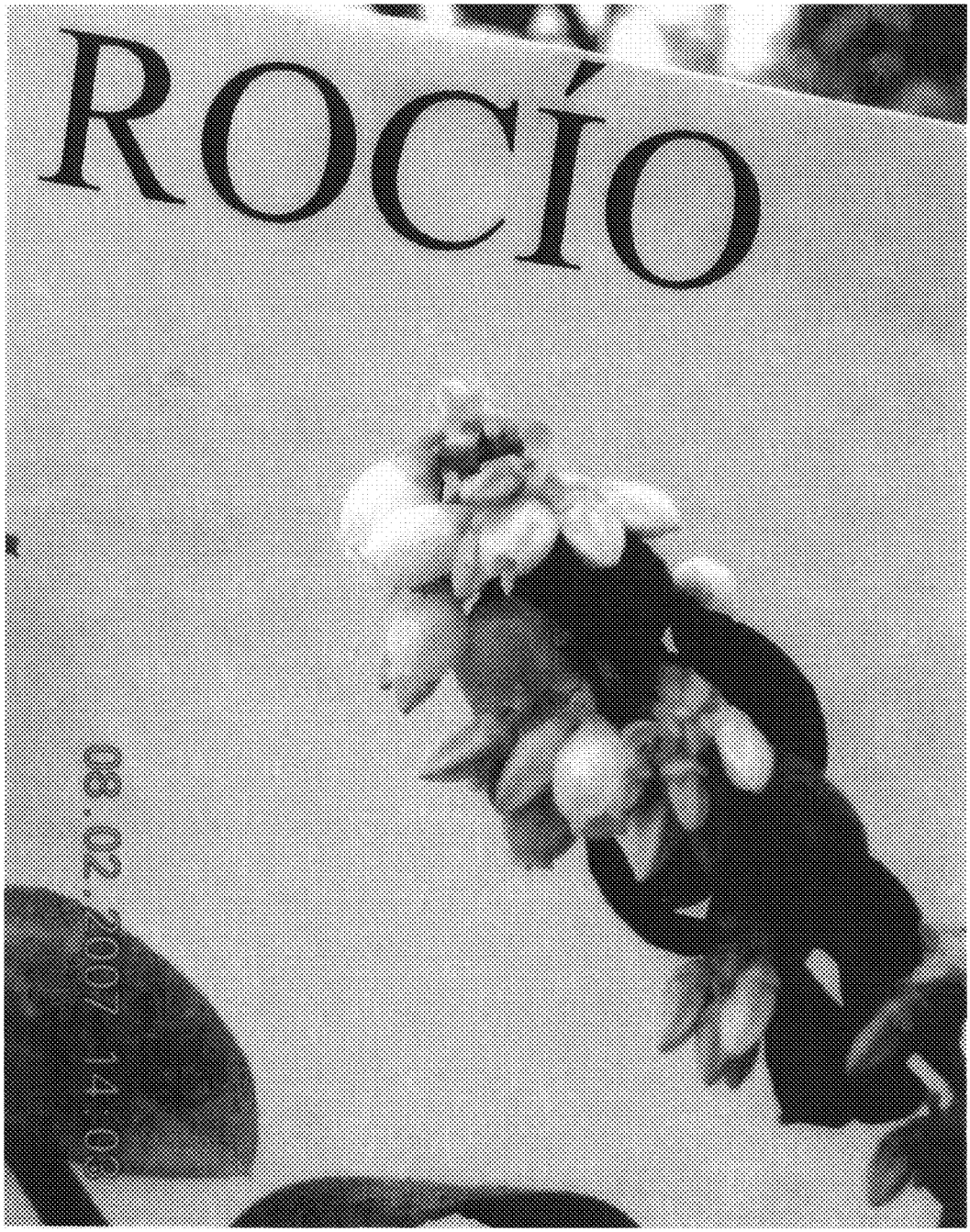
Figure 3:
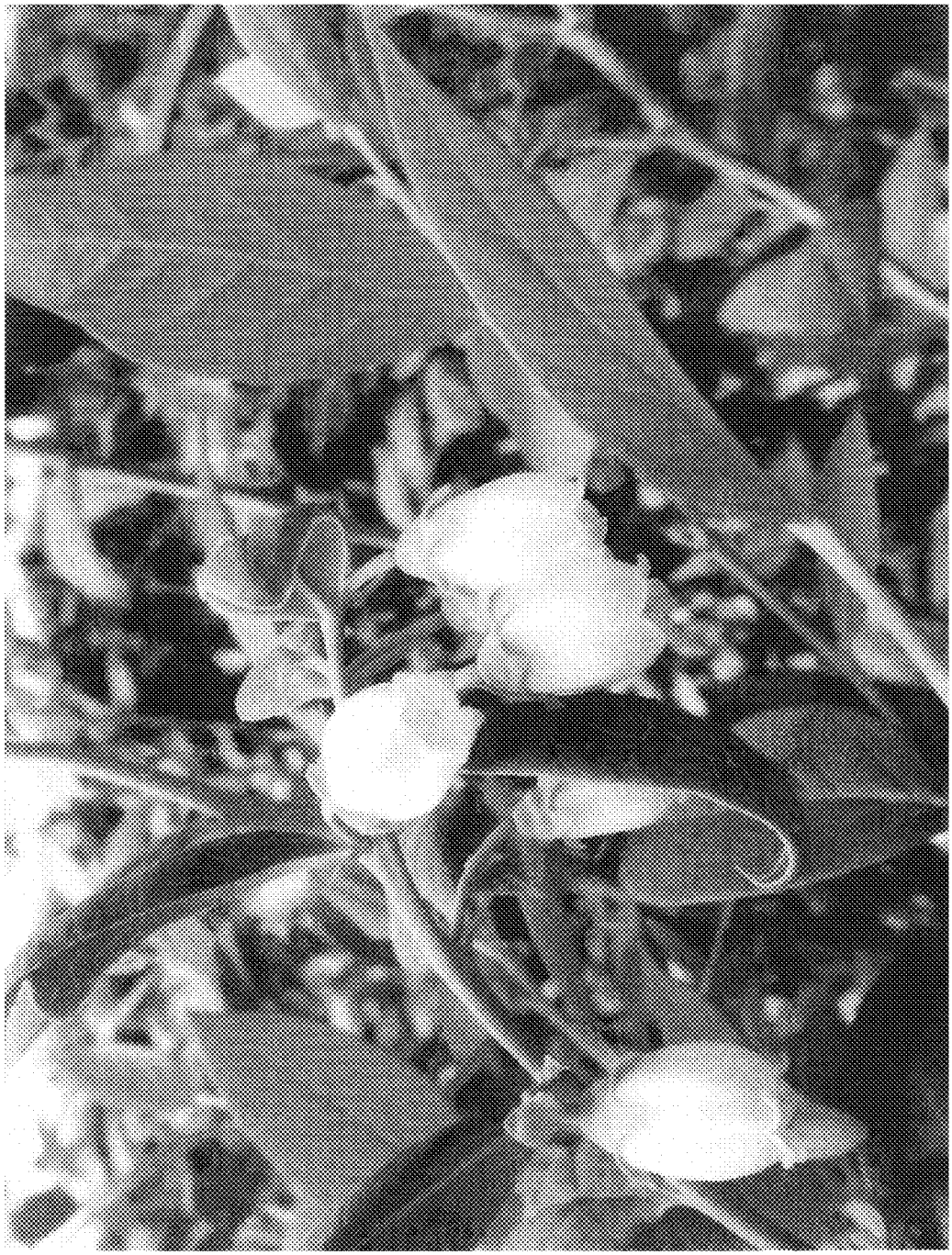
FIG. 3 shows a close view of typical foliage (both surfaces) and typical flowers of the new cultivar.
Figure 4:
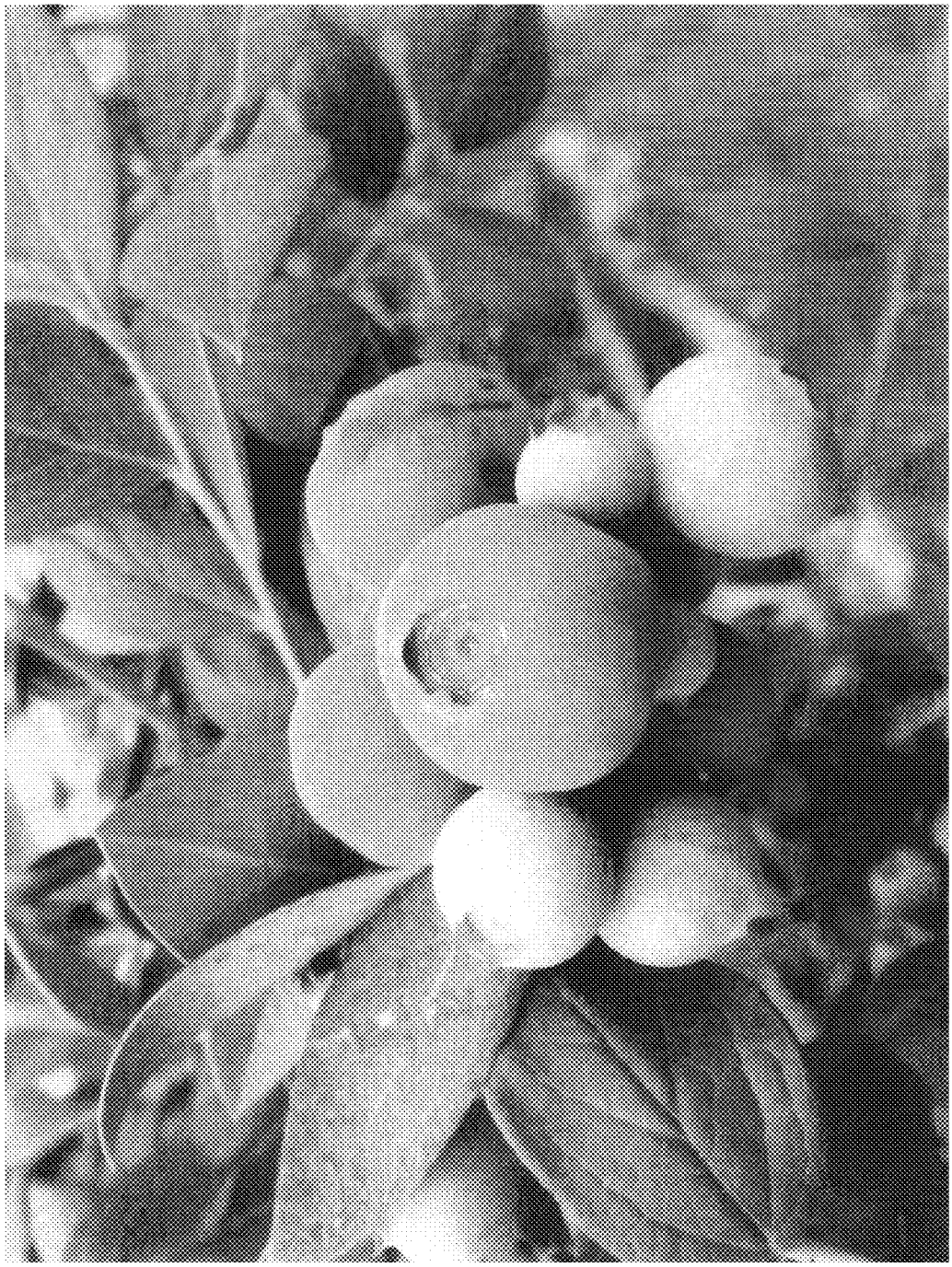
FIG. 4 shows typical berries of the new cultivar in various stages of maturity as well as the foliage of the new cultivar.
Figure 5:
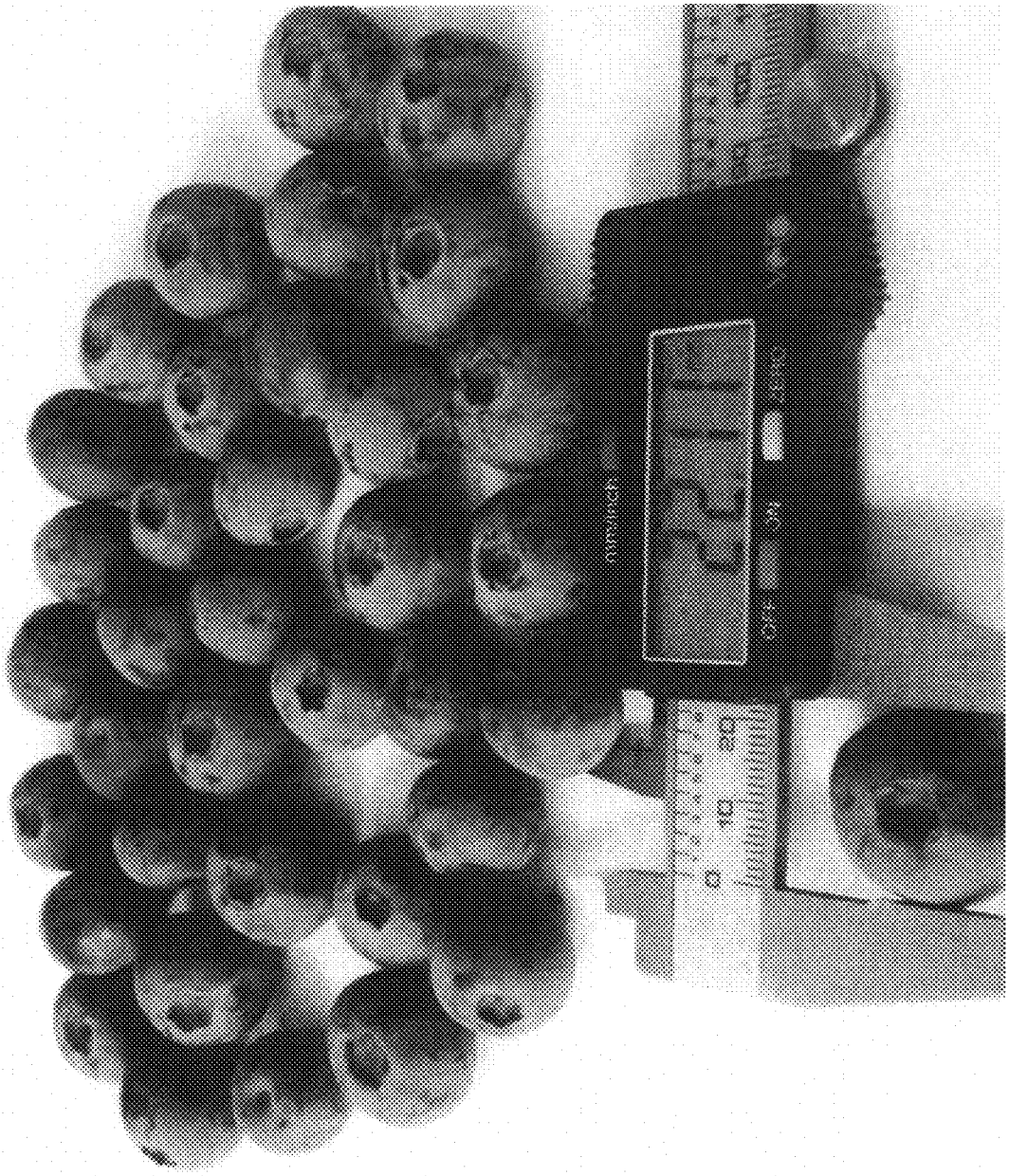
FIG. 5 shows an array of typical mature berries of the new cultivar together with a basis for size comparison.
Figure 6:
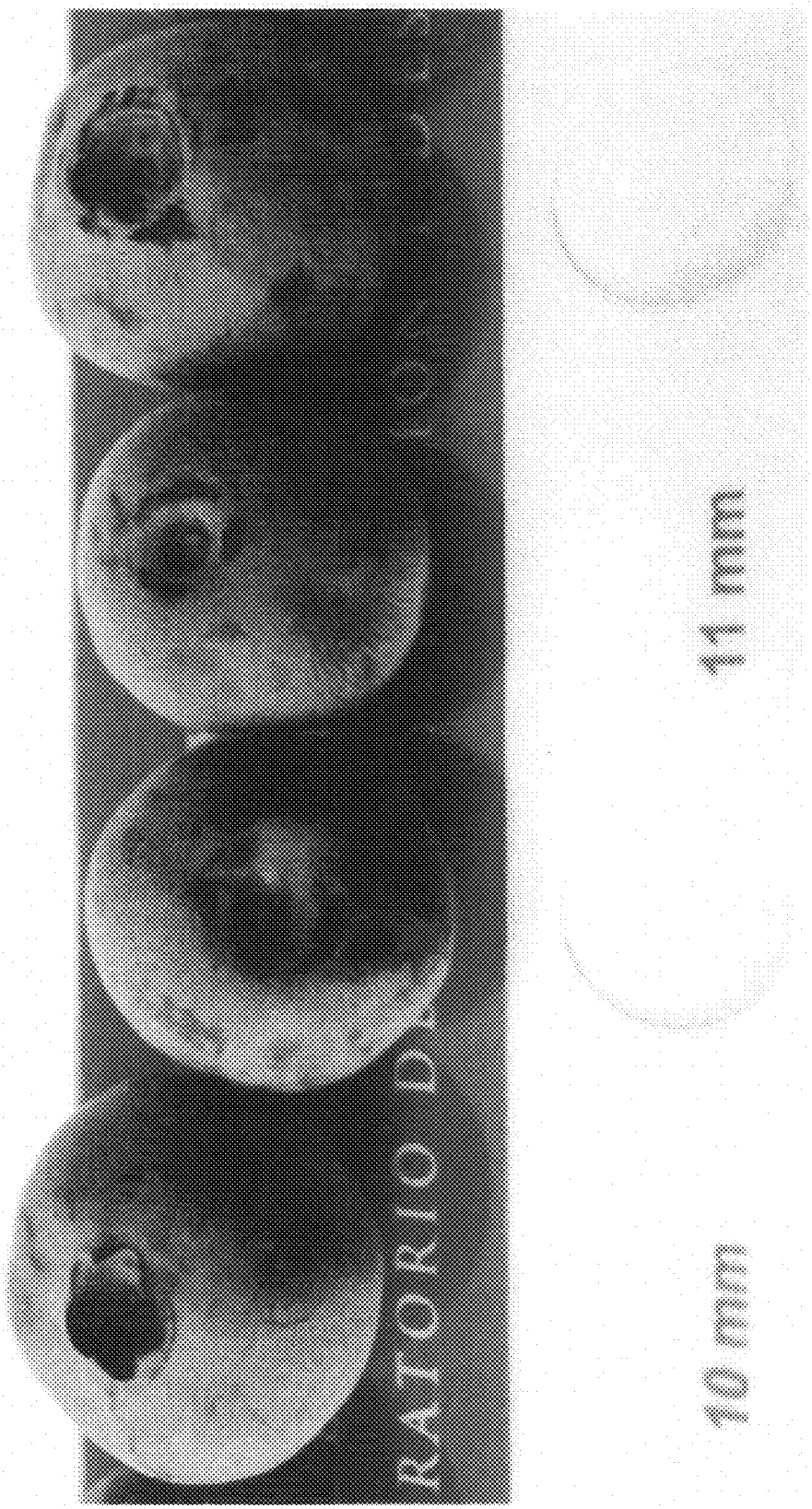
FIG. 6 shows a close view of typical mature berries of the new cultivar together with a further basis for size comparison.

The chart used in the identification of the colors described herein is The R.H.S. Colour Chart of The Royal Horticultural Society, London, England. Ordinary color terms are to be accorded their customary dictionary significance. The description is based on the observation primarily during March–April 2008 of approximately five-year-old plants of the new cultivar which had been asexually reproduced by the rooting of cuttings while growing outdoors at Almonte, Huelva, Spain.

Plant:

*Growth habit.*—Generally vase to upright.

*Height.*—Approximately 1.8 m at 5 years of age.

*Width.*—Approximately 3 m at 5 years of age.

*One-year canes.*—Commonly measure approximately 89.6 cm in length on average, approximately 10.6 mm in diameter on average at the base, approximately 5.2 mm in diameter on average near the tip, and commonly are near Yellow-Green Group 144B in coloration on a five-year-old plant.

*Five-year canes.*—Available five-year-old canes which had undergone some pruning have been found to measure approximately 72.0 cm in length on average, approximately 28.8 mm in diameter on average at the base, approximately 20.8 mm in diameter on average near the tip, and commonly are near Grey-Brown Group 199D in coloration.

*Foliage retention.*—Evergreen.

*Chill requirement.*—Less than 300 hours.

Foliage:

*Shape.*—Elliptic-obovate to elliptic.

*Length.*—Commonly approximately 84 mm on average.

*Width.*—Commonly approximately 38 mm on average.

*Apex.*—Acute.

*Base.*—Acute.

*Margin.*—Entire.

*Texture.*—Glabrous and non-glandular.

*Color.*—Yellow-Green Group 147A on the upper (adaxial) surface, and Green Group 138C on the under (abaxial) surface.

Flowers:

*Time.*—Very early, at Almonte, Huelva, Spain, with first flower commonly at approximately November 10$^{th}$, and 50 percent bloom at approximately February 10$^{th}$.

*Number.*—Commonly approximately 5.5 flowers per bud on average.

*Color.*—When immature Green-White Group 157C with some Green Group 142C, and when mature Green-White Group 157D.

*Length.*—Commonly approximately 13 mm on average.

*Corolla tube width.*—Commonly approximately 8 mm on average at the widest point.

*Petals.*—5 in number.

*Petal size.*—Commonly approximately 10 mm in length on average, and approximately 4 mm in width on average.

*Pistil.*—Bottle-shaped with narrowing towards the tip, approximately 0.5 to 1 mm in thickness at the base, the style length is approximately 9.5 mm on average, and the coloration is light green with slightly darker green at the base and stigma.

*Stamen.*—Filaments possess pubescence and are light green in coloration, anthers are bronze in coloration with a slightly darker pollen sack, and approximately 30 percent of the filaments are fused.

*Fertility.*—Self-fertile.

*Fragrance.*—Pleasant fragrance.

Fruit:

*Time.*—Commonly from approximately March 1$^{st}$ to May 10$^{th}$ at Almonte, Huelva, Spain (i.e., approximately 10 weeks).

*Shape.*—Generally pumpkin-shaped (as illustrated).

*Height.*—Commonly approximately 16 mm on average.

*Width.*—Commonly approximately 19 mm on average.

*Weight.*—Approximately 2.55 g/berry on average during 2007 when plants were 4 years of age.

*Fruit scar.*—Approximately 1.5 mm in size.

*Fruit scar tear.*—Substantially none.

*Seed number.*—Commonly approximately 20 per berry on average.

*Seed size.*—Commonly approximately 1.5 mm in length and approximately 1 mm in width on average.

*Immature color.*—Commonly near Green Group 142D with bloom and Yellow-Green Group 145B without bloom.

*Mature color.*—Commonly near Violet-Blue Group 97B with bloom and Black Group 202A without bloom.

*Productivity.*—Approximately 3.84 Kg/plant on average during 2007 when plants were 4 years of age.

*Firmness.*—Extremely firm which enables totally ripe fruit to hang on the tree for 10 days or more in the absence of any substantial quality deterioration.

*Flavor.*—Excellent with a satisfactory balance of acid-sweetness.

Development:

*Ability to store.*—The fruit stores well under refrigeration.

*Disease tolerance.*—No special sensitivity to common Blueberry diseases has been encountered during observations to date at Almonte, Huelva, Spain, and has shown less susceptibility to common stem blight than the 'Sharpblue' cultivar (non-patented in the United States).

*Insects.*—Is susceptible to aphids and thrips.

*Cultural conditions.*—Does well in well drained soils and evergreen growing conditions in a low-chilling area.

Plants of the 'Rocio' cultivar have not been observed under all possible environmental conditions to date, Accordingly, it is possible that the phenotypic expression may vary somewhat with changes in light intensity and duration, cultural practices, and other environmental conditions without variance in the genotype.

We claim:

1. A new and distinct Blueberry plant that possess the following combination of characteristics:

(a) flowers very early and forms fruit that ripens very early, (b) displays a generally vase to upright growth habit with attractive evergreen foliage, (c) is self-fertile, (d) displays a low chilling requirement, and (e) forms in abundance extremely firm violet-blue berries that exhibit an excellent balance of acid-sweetness;

substantially as herein shown and described.

* * * * *